(12) United States Patent
Lloyd et al.

(10) Patent No.: US 8,038,656 B2
(45) Date of Patent: Oct. 18, 2011

(54) DETACHABLE PLUNGER ROD SYRINGE

(75) Inventors: Ronald Lloyd, DeLand, FL (US); Ellen Morefield, DeLand, FL (US); Eric Sampson, DeLand, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 204 days.

(21) Appl. No.: 11/862,718

(22) Filed: Sep. 27, 2007

(65) Prior Publication Data
US 2008/0082055 A1    Apr. 3, 2008

Related U.S. Application Data

(60) Provisional application No. 60/848,566, filed on Sep. 29, 2006.

(51) Int. Cl.
*A61M 5/315* (2006.01)
(52) U.S. Cl. .............. 604/228; 604/218; 604/229
(58) Field of Classification Search .............. 604/110, 604/118, 218, 228, 229
See application file for complete search history.

(56) References Cited

U.S. PATENT DOCUMENTS

| | | | |
|---|---|---|---|
| 729,011 A | 5/1903 | Tagliabue et al. | |
| 2,688,325 A | 9/1954 | Lockhart | |
| 3,128,765 A | 4/1964 | Tint | |
| 3,811,441 A | 5/1974 | Sarnoff | |
| 3,820,652 A | 6/1974 | Thackston | |
| 3,890,971 A | 6/1975 | Leeson et al. | |
| 4,144,885 A | 3/1979 | Stait | |
| 4,197,846 A | 4/1980 | Bucalo | |
| 4,252,118 A | 2/1981 | Richard et al. | |
| 4,367,738 A | 1/1983 | Legendre et al. | |
| 4,391,272 A | 7/1983 | Staempfli | |
| 4,493,703 A | 1/1985 | Butterfield | |
| 4,675,005 A | 6/1987 | DeLuccia | |
| 4,677,980 A | 7/1987 | Reilly et al. | |
| 4,685,910 A | 8/1987 | Schweizer | |
| 4,699,614 A | 10/1987 | Glazier | |
| 4,713,056 A | 12/1987 | Butterfield | |
| 4,731,068 A | 3/1988 | Hesse | |
| 4,781,684 A | 11/1988 | Trenner | |
| 4,834,717 A | 5/1989 | Haber et al. | |

(Continued)

OTHER PUBLICATIONS

International Search Report from International Application No. PCT/US2007/021008 dated Apr. 16, 2008.

*Primary Examiner* — Bhisma Mehta
*Assistant Examiner* — Larry R Wilson
(74) *Attorney, Agent, or Firm* — Lisa E. Winsor, Esq.

(57) ABSTRACT

A plunger rod assembly for use with a syringe barrel is provided and includes a plunger rod slidably disposable within the syringe barrel, wherein the plunger rod includes a hub extending distally from a distal end thereof and at least two tabs extending outwardly therefrom. The syringe further includes a plug configured for slidable disposition in the syringe barrel and configured for selective connection to the plunger rod via a bayonet-type engagement. The plug includes a base wall having at least two resilient fingers supported on a first side thereof, wherein each resilient finger is configured to snap-fit engage a respective tab of the plunger rod during connection of the plug to the plunger rod; and a plunger tip supported on a second side of the base wall, opposite the first side, and being configured to form a substantially fluid tight seal with an inner surface of the syringe barrel.

21 Claims, 10 Drawing Sheets

U.S. PATENT DOCUMENTS

| | | | |
|---|---|---|---|
| 4,906,231 A | 3/1990 | Young | |
| 4,908,020 A | 3/1990 | Pettersen | |
| 4,911,695 A * | 3/1990 | Lindner | 604/228 |
| 4,932,941 A | 6/1990 | Min et al. | |
| 4,936,315 A | 6/1990 | Lineback | |
| 4,950,240 A | 8/1990 | Greenwood et al. | |
| 4,969,877 A | 11/1990 | Kornberg | |
| 4,973,309 A | 11/1990 | Sultan | |
| 5,004,460 A | 4/1991 | Gimeno | |
| 5,007,904 A | 4/1991 | Densmore et al. | |
| 5,032,114 A | 7/1991 | Olovson | |
| 5,059,179 A | 10/1991 | Quatrochi et al. | |
| 5,084,017 A * | 1/1992 | Maffetone | 604/110 |
| 5,085,638 A | 2/1992 | Farbstein et al. | |
| 5,090,962 A | 2/1992 | Landry, Jr. et al. | |
| 5,094,148 A | 3/1992 | Haber et al. | |
| 5,106,372 A | 4/1992 | Ranford | |
| 5,127,906 A | 7/1992 | Landry, Jr. et al. | |
| 5,135,495 A | 8/1992 | Arcusin | |
| 5,171,300 A | 12/1992 | Blake, III et al. | |
| 5,181,912 A | 1/1993 | Hammett | |
| 5,195,975 A | 3/1993 | Castagna | |
| 5,215,536 A | 6/1993 | Lampropoulos et al. | |
| 5,238,003 A | 8/1993 | Baidwan et al. | |
| 5,242,400 A | 9/1993 | Blake, III et al. | |
| 5,257,976 A | 11/1993 | Fenet | |
| 5,328,484 A | 7/1994 | Somers et al. | |
| 5,336,189 A | 8/1994 | Sealfon | |
| 5,338,303 A | 8/1994 | King et al. | |
| 5,352,200 A | 10/1994 | Hammett et al. | |
| 5,364,359 A | 11/1994 | van den Haak | |
| 5,385,558 A | 1/1995 | Cottone, Sr. et al. | |
| 5,397,313 A | 3/1995 | Gross | |
| 5,411,488 A | 5/1995 | Pagay et al. | |
| 5,411,489 A | 5/1995 | Pagay et al. | |
| 5,413,563 A | 5/1995 | Basile et al. | |
| 5,423,757 A * | 6/1995 | Olovson et al. | 604/110 |
| 5,478,314 A | 12/1995 | Malenchek | |
| 5,490,842 A | 2/1996 | Volk et al. | |
| 5,496,285 A | 3/1996 | Schumacher et al. | |
| 5,531,255 A | 7/1996 | Vacca | |
| 5,531,693 A | 7/1996 | Vounatsos | |
| 5,536,253 A | 7/1996 | Haber et al. | |
| 5,582,595 A | 12/1996 | Haber et al. | |
| 5,593,386 A | 1/1997 | Helldin | |
| 5,624,408 A | 4/1997 | Helldin | |
| 5,662,612 A | 9/1997 | Niehoff | |
| 5,718,690 A | 2/1998 | Gettig | |
| 5,735,825 A | 4/1998 | Stevens et al. | |
| 5,772,687 A | 6/1998 | Saito | |
| 5,782,815 A | 7/1998 | Yanai et al. | |
| RE35,979 E | 12/1998 | Reilly et al. | |
| 5,860,961 A | 1/1999 | Gettig | |
| 5,873,861 A | 2/1999 | Hitchins et al. | |
| 5,879,339 A | 3/1999 | Saito | |
| D412,206 S | 7/1999 | Basile et al. | |
| 5,919,167 A | 7/1999 | Mulhauser et al. | |
| 5,928,202 A | 7/1999 | Linnebjerg | |
| 5,947,935 A | 9/1999 | Rhinehart et al. | |
| 5,951,527 A | 9/1999 | Sudo | |
| 6,004,300 A | 12/1999 | Butcher et al. | |
| 6,017,330 A | 1/2000 | Hitchins et al. | |
| 6,059,756 A | 5/2000 | Yeh | |
| 6,090,081 A | 7/2000 | Sudo et al. | |
| 6,123,687 A | 9/2000 | Simonyi et al. | |
| 6,129,712 A | 10/2000 | Sudo et al. | |
| 6,156,013 A | 12/2000 | Mahurkar | |
| 6,162,200 A | 12/2000 | Sawa et al. | |
| 6,171,286 B1 | 1/2001 | Gross | |
| 6,196,999 B1 | 3/2001 | Goethel et al. | |
| 6,206,856 B1 | 3/2001 | Mahurkar | |
| 6,264,620 B1 | 7/2001 | Shieh | |
| 6,391,008 B1 | 5/2002 | Tsai | |
| 6,402,721 B1 | 6/2002 | Lo | |
| 6,409,704 B1 | 6/2002 | Tsai | |
| 6,432,089 B1 | 8/2002 | Kakimi et al. | |
| 6,488,651 B1 | 12/2002 | Morris et al. | |
| 6,488,657 B1 | 12/2002 | Lo | |
| 6,494,866 B1 | 12/2002 | Robinson | |
| 6,533,758 B1 | 3/2003 | Staats et al. | |
| 6,565,529 B1 | 5/2003 | Kimber et al. | |
| 6,582,399 B1 | 6/2003 | Smith et al. | |
| 6,648,851 B2 | 11/2003 | Pyret et al. | |
| 6,663,593 B2 | 12/2003 | Ito | |
| 6,676,642 B2 | 1/2004 | Beebe | |
| 6,733,475 B2 | 5/2004 | Huang et al. | |
| 6,752,789 B2 | 6/2004 | Duchon et al. | |
| 6,764,466 B1 | 7/2004 | Staats et al. | |
| 6,773,416 B1 | 8/2004 | Hsu | |
| 6,817,990 B2 | 11/2004 | Yap et al. | |
| 6,835,191 B2 | 12/2004 | Lee et al. | |
| 6,846,301 B2 | 1/2005 | Smith et al. | |
| 6,872,191 B2 | 3/2005 | Lo | |
| 6,953,449 B2 | 10/2005 | Huang | |
| 6,976,975 B2 | 12/2005 | Hsieh et al. | |
| 6,979,314 B2 | 12/2005 | Hsieh et al. | |
| 7,056,301 B2 | 6/2006 | Liu | |
| 2002/0022807 A1 | 2/2002 | Duchon et al. | |
| 2002/0128609 A1 * | 9/2002 | Koch et al. | 604/218 |
| 2002/0133138 A1 | 9/2002 | Pyret et al. | |
| 2004/0006308 A1 | 1/2004 | Lo | |
| 2004/0082911 A1 | 4/2004 | Tiu et al. | |
| 2004/0111063 A1 | 6/2004 | Botich et al. | |
| 2004/0167004 A1 | 8/2004 | Jorgensen et al. | |
| 2004/0176722 A1 | 9/2004 | Capes et al. | |
| 2005/0015056 A1 | 1/2005 | Duchon et al. | |
| 2005/0049554 A1 | 3/2005 | Chueh | |
| 2005/0054979 A1 | 3/2005 | Liu | |
| 2005/0065479 A1 | 3/2005 | Schiller et al. | |
| 2005/0113751 A1 | 5/2005 | Chen | |
| 2005/0137533 A1 | 6/2005 | Sudo et al. | |
| 2005/0154353 A1 | 7/2005 | Alheidt | |
| 2005/0177107 A1 | 8/2005 | Dugmore et al. | |
| 2005/0240149 A1 | 10/2005 | Lu | |
| 2006/0084915 A1 | 4/2006 | Chang | |
| 2006/0084917 A1 | 4/2006 | Chen | |
| 2006/0106341 A1 | 5/2006 | Lou | |

* cited by examiner

DETACHABLE PLUNGER ROD SYRINGE

CROSS-REFERENCE TO RELATED APPLICATION

The present application claims the benefit of and priority to U.S. Provisional Application Ser. No. 60/848,566, filed on Sep. 29, 2006, the entire content of which is incorporated herein by reference.

BACKGROUND

1. Technical Field

The present disclosure relates to syringes and, more particularly, to medical syringes such as disposable syringes and prefilled syringes, which are discarded after a single administration and which include a selectively attachable/detachable plunger rod.

2. Background of Related Art

A conventional syringe typically comprises a hollow barrel configured to slidably receive a plunger having a piston supported on a distal end thereof. The plunger is received in the hollow barrel and partially extends through a proximal end of the hollow barrel. In use, as the plunger is translated relative to the hollow barrel, the piston is also translated to thereby withdraw and/or expel fluid into/out of the hollow barrel.

In the case of pre-filled syringes, the syringe is provided a barrel containing a fluid and with the plunger pre-attached to the barrel. In the instance of relatively large pre-filled syringes, the portion of the plunger extending from the barrel may be relatively large. Accordingly, in order to reduce the overall length of the pre-filled barrel and plunger, in order to minimize storage and shipping costs, pre-filled syringes have been developed wherein the plunger is selectively attachable/detachable to/from the piston. In this manner, syringes comprising pre-filled barrels and separate plungers, may be stored and shipped at reduced costs.

In view of the foregoing, a need exists for improved syringes incorporating plungers which are selectively attachable/detachable to/from a piston.

SUMMARY

The present disclosure relates to medical syringes such as disposable syringes and prefilled syringes, which are discarded after a single administration and which include a selectively attachable/detachable plunger rod.

According to an embodiment of the present disclosure, a syringe is provided and includes a syringe barrel having a distal end, a proximal end and defining a cavity therebetween; and a plunger rod slidably disposed within the cavity of the syringe barrel, wherein the plunger rod includes a plunger shaft having a hub extending distally from a distal end thereof, and wherein the hub includes at least two tabs extending outwardly therefrom. The syringe further includes a plug configured for slidable disposition in the cavity of the syringe barrel and configured for selective connection to the hub of the plunger rod. The plug includes a base wall having at least two spaced apart uprights extending from a first side thereof, wherein each upright includes a resilient finger formed therein, each resilient finger is configured to snap-fit engage a respective tab of the plunger rod during connection of the plug to the plunger rod; and a plunger tip supported on a second side of the base wall, opposite the first side, and being configured to form a substantially fluid tight seal with an inner surface of the cavity of the syringe barrel.

Each resilient finger may include a shoulder extending inwardly therefrom. Each shoulder may include a sloping distal surface. Each shoulder may include a substantially orthogonal surface formed therein for inhibiting a respective tab of the plunger rod from moving therebeyond, whereby disconnection of the plug from the plunger rod is prevented. Each resilient finger may define a recess formed in an inner surface thereof which defines the substantially orthogonal surface.

At least one tab may include a stop member configured to engage the substantially orthogonal surface of a respective resilient finger.

The tabs of the plunger rod may be diametrically opposed from one another. The tabs of the plunger rod may extend substantially radially outward from the hub. The tabs and the hub of the plunger rod may define a substantially planar distal surface.

At least one upright may include a stop extending from an inner surface thereof for preventing movement of the tabs of the plunger rod as the plunger rod is rotated with respect to the plug.

The plunger tip may be formed of an elastomeric material. The base wall and the uprights of the plug may be formed from polypropylene.

The plug may be connected to the distal end of the plunger rod in a bayonet-type connection.

According to another aspect of the present disclosure, a plunger rod assembly for use with a syringe barrel is provided and includes a plunger rod slidably disposable within the syringe barrel, wherein the plunger rod includes a hub extending distally from a distal end thereof and at least two tabs extending outwardly therefrom. The syringe further includes a plug configured for slidable disposition in the syringe barrel and configured for selective connection to the plunger rod via a bayonet-type engagement. The plug includes a base wall having at least two resilient fingers supported on a first side thereof, wherein each resilient finger is configured to snap-fit engage a respective tab of the plunger rod during connection of the plug to the plunger rod; and a plunger tip supported on a second side of the base wall, opposite the first side, and being configured to form a substantially fluid tight seal with an inner surface of the syringe barrel.

Each resilient finger may include a shoulder extending inwardly therefrom. Each shoulder may include a substantially orthogonal surface formed therein for inhibiting a respective tab of the plunger rod from moving therebeyond, whereby disconnection of the plug from the plunger rod is prevented. Each resilient finger may define a recess formed in an inner surface thereof and may define the substantially orthogonal surface. The at least one tab may include a stop member configured to engage the substantially orthogonal surface of a respective resilient finger.

The at least one upright may include a stop extending from an inner surface thereof for preventing movement of the tabs of the plunger rod as the plunger rod is rotated with respect to the plug.

According to a further embodiment of the present disclosure, a syringe is provided which includes a syringe barrel having a distal end, a proximal end and defining a cavity therebetween; and a plunger rod slidably disposable within the cavity of the syringe barrel, wherein the plunger rod includes a plunger shaft having a hub extending distally from a distal end thereof. The hub includes a pair of tabs extending outwardly therefrom. The syringe further includes a plug configured for slidable disposition in the cavity of the syringe barrel and configured for selective connection to the distal end of the plunger rod via a bayonet-type engagement. The plug includes a base wall having a pair of spaced apart uprights extending from a first side thereof, wherein each upright includes a resilient finger formed therein, each resilient finger is configured to snap-fit engage a respective tab of the plunger rod as the plunger rod is rotated with respect to the plug when the pair of tabs are in registration with the respective resilient fingers; and a plunger tip supported on a second side of the base wall, opposite the first side, and being configured to form at least a substantially fluid tight seal with an inner surface of the cavity of the syringe barrel.

DETAILED DESCRIPTION OF THE DRAWINGS

DETAILED DESCRIPTION OF THE EMBODIMENTS

Figures 1, 1A:
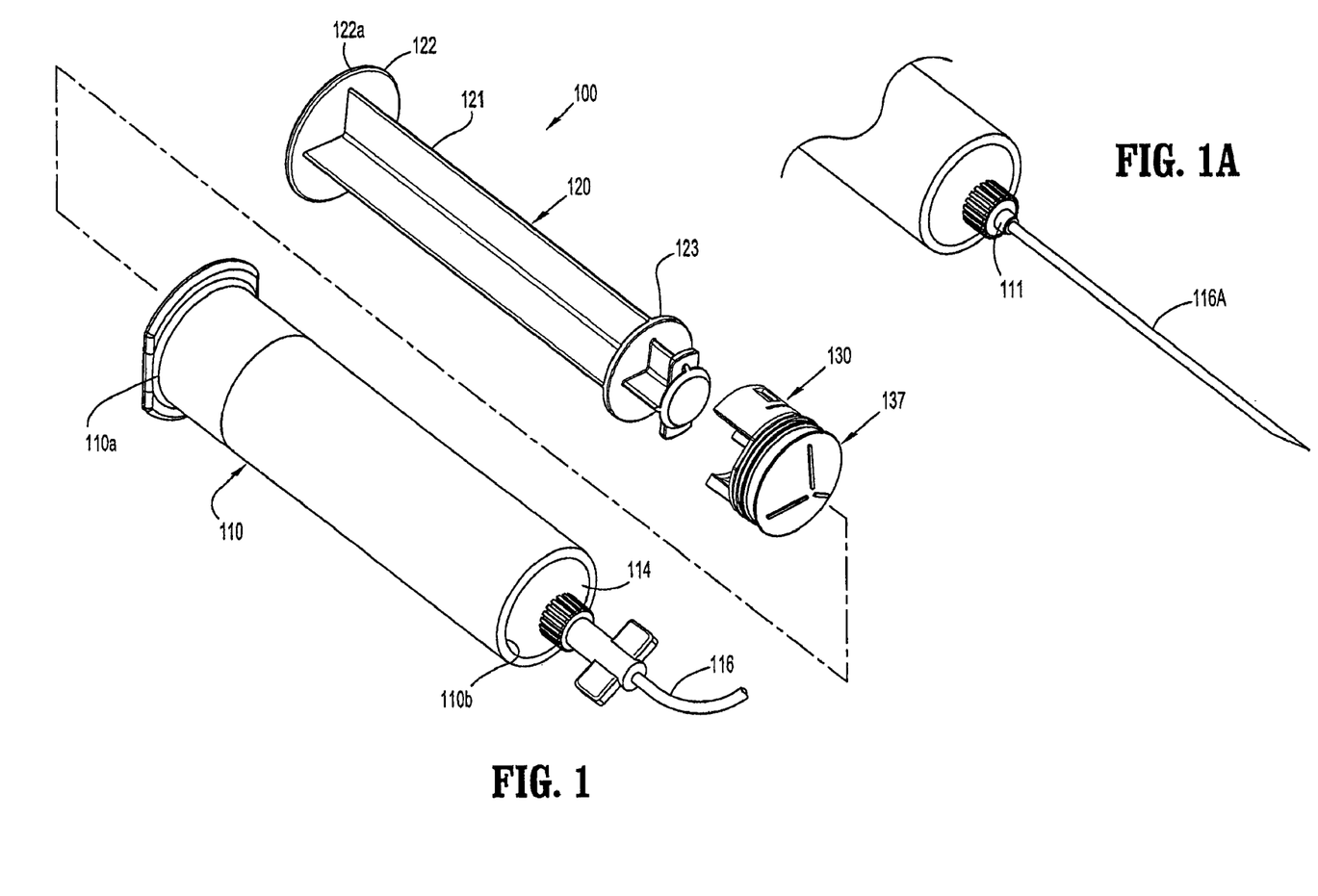
FIG. 1 is a perspective view, with parts separated, of a detachable plunger rod syringe according to an embodiment of the present disclosure.
FIG. 1A is a perspective view of a distal end of the detachable plunger rod syringe of FIG. 1 including a needle secured thereto.
Figure 2:
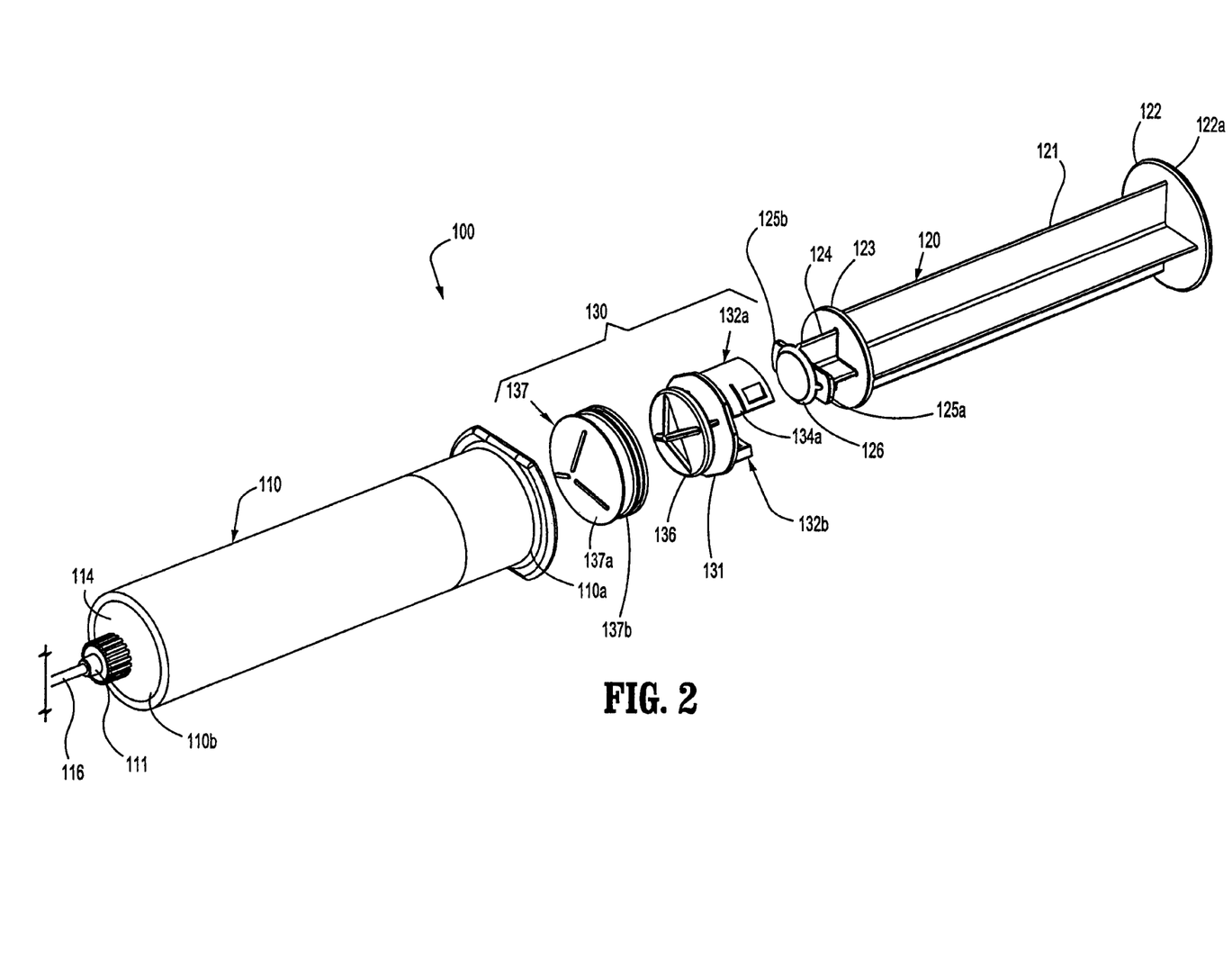
FIG. 2 is an exploded perspective view of the detachable plunger rod syringe of FIG. 1.

As seen in FIGS. 1-13, a medical-type detachable plunger rod syringe used in the administration of fluids, is generally designated as 100. As seen in FIGS. 1 and 2, the detachable plunger rod syringe 100 includes a syringe barrel 110, a plunger rod 120 slidably disposable within syringe barrel 110, and a plug 130 selectively supportable on a distal end of plunger rod 120.

As seen in FIGS. 1 and 2, syringe barrel 110 includes a proximal end 110a, a distal end 110b, and defines a cavity 110c (see FIGS. 8, 12 and 13) therebetween. Distal end 110b includes an elongate barrel tip 111 (see FIGS. 8 and 13). Elongate barrel tip 111 is in fluid communication with cavity 110c of syringe barrel 110.

Syringe barrel 110 defines a distal frusto-conical surface 114 between distal end 110b thereof and barrel tip 111. As seen in FIG. 8, barrel tip 111 has a frusto-conical configuration defining a tapered outer surface 111a and a tapered inner surface 111b to form a standard luer fitting.

As seen in FIGS. 1 and 2, a syringe tube set including a tube 116 is supported on barrel tip 111 via a fluid tight coupling therebetween. Syringe tube 116 defines a lumen extending therethrough (not shown) for fluid communication with cavity 110c of syringe barrel 110.

Alternatively, as seen in FIG. 1A, a syringe needle 116a may be supported on barrel tip 111. In this manner, syringe 100 may be used to percutaneously or otherwise penetrate tissue and the like to deliver medicament or other beneficial fluids and/or to withdraw fluids as needed and/or desired.

Figure 6:
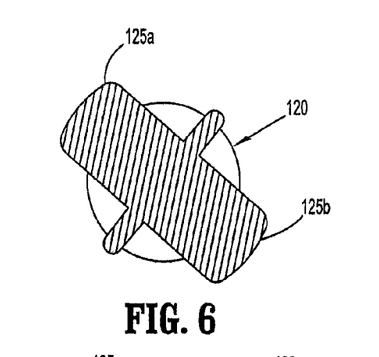
FIG. 6 is a distal end view of the plunger rod of the detachable plunger rod syringe of FIGS. 1 and 2.
Figure 7:
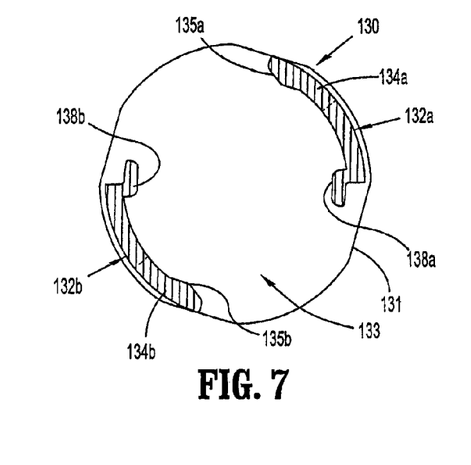
FIG. 7 is a top plan view of the plug of the detachable plunger rod syringe of FIGS. 1 and 2.
Figures 7A, 8:
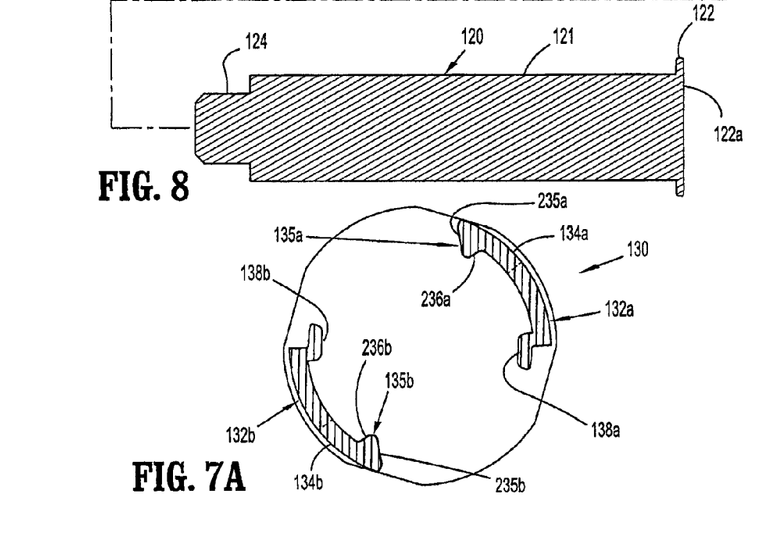
FIG. 7A is a top plan view of a plug, according to another embodiment, of the detachable plunger rod syringe of FIGS. 1 and 2.
FIG. 8 is a longitudinal, cross-sectional view of the detachable plunger rod syringe of FIGS. 1 and 2, with the plug disposed within the syringe barrel and the plunger rod separated therefrom.

With continued reference to FIGS. 1 and 2 above, as well as FIGS. 6-8, syringe 100 further includes a plunger rod 120 having an elongate plunger shaft 121 configured and dimensioned for slidable disposition within cavity 110c of syringe barrel 110. Plunger shaft 121 includes a proximal end 122 which extends out of proximal end 110a of syringe barrel 110 and defines a finger engagement surface 122a. Plunger shaft 121 includes a distal end 123 disposable within cavity 110c of syringe barrel 110.

Distal end 123 of plunger shaft 121 is configured and dimensioned to support plug 130 thereon. Distal end 123 includes a hub 124 extending distally therefrom and a pair of tabs 125a, 125b extending radially outwardly from hub 124. Each tab 125a, 125b has a length which extends radially beyond an outer diameter of hub 124 and which length does not extend radially beyond an inner diameter of cavity 110c of syringe barrel 110. Hub 124 includes a spacer 126 disposed distally of tabs 125a, 125b.

As seen in FIGS. 2-5 and 9-11, plug 130 includes a base wall 131 having a pair of spaced apart uprights 132a, 132b extending from a first surface thereof. Uprights 132a, 132b define a space 133 therebetween (see FIGS. 3 and 7). Each upright 132a, 132b includes a resilient finger 134a, 134b, respectively formed therein. As seen in FIGS. 3-5, 7 and 9-11 below, each resilient finger 134a, 134b includes a shoulder 135a, 135b, respectively, extending radially inward therefrom and formed proximate a free end thereof. Shoulders 135a, 135b function to snap-fit over respective tabs 125a, 125b of plunger rod 120 during attachment and detachment of plug 130 to distal end 123 of plunger rod 120.

As seen in FIGS. 7 and 9-11, shoulders 135a, 135b have a sloping profile to enable attachment and detachment of plunger rod 120 to plug 130. Alternatively, as seen in FIGS. 7A and 11A, shoulders 135a, 135b may have a distal surface 235a, 235b having a sloping profile and a proximal surface 236a, 236b having a substantially orthogonal profile. In this manner, plunger rod 120 may be relatively easily attached to plug 130, however, plunger rod 120 may not be relatively easily detached from plug 130. In particular, as plunger rod 120 is rotated relative to plug 130, tabs 125a, 125b cam against respective distal surfaces 235a, 235b to radially extend fingers 134a, 134b and snap-fit behind respective proximal surfaces 236a, 236b. In this manner, proximal surfaces 236a, 236b prevent fingers 134a, 134b from extending radially outward upon a rotation of plunger rod 120, in a direction opposite to the direction of attachment, in order to detach plunger rod 120 from plug 130.

As seen in FIGS. 1, 2, 8 and 13, plug 130 includes a support element 136 extending from a second surface of base wall 131, opposite the first surface. Plug 130 further includes a resilient plunger tip 137 supported on support element 136 thereof. Plunger tip 137 includes a distal surface 137a having a substantially conical profile and a proximal surface (not shown) configured and adapted to selectively engage with support element 136 of plug 130 in a snap-over-type engagement. Plunger tip 137 defines at least one annular rib 137b for creating a fluid tight engagement with an inner surface of syringe barrel 110 when plunger tip 137 is disposed within cavity 110c thereof.

Base wall 131, uprights 132a, 132b and/or support element 136 may be formed of a semi-rigid material, such as polypropylene. Plunger tip 137 may be formed of a resilient and/or elastomeric material, such as, for example, rubber or silicone rubber.

Figure 3:
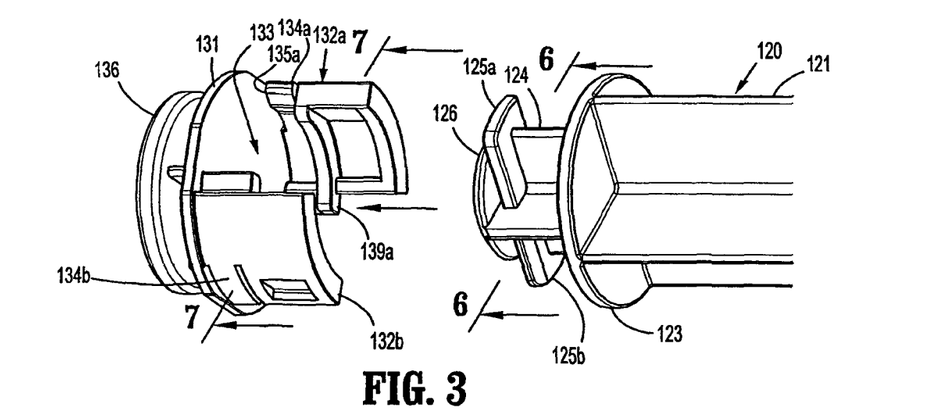
FIGS. 3-5 are perspective views illustrating the attachment of the plunger rod to the plug of the detachable plunger rod syringe of FIGS. 1 and 2.
Figure 4:
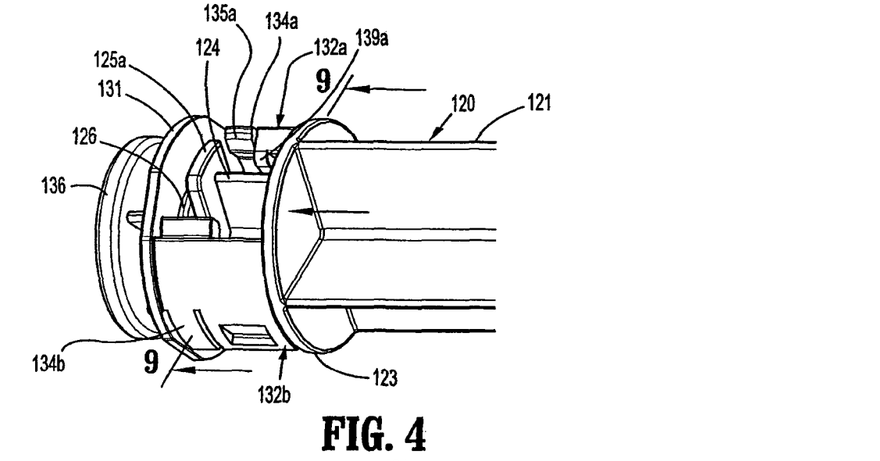
Figure 5:
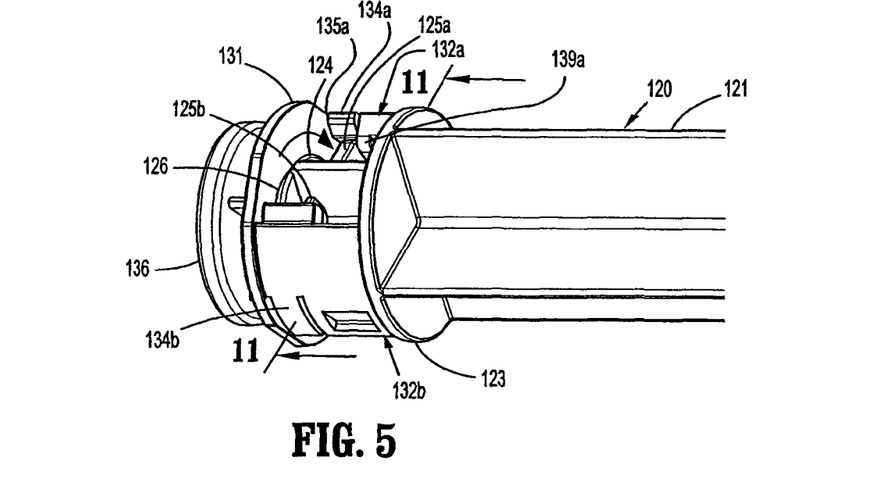
Figure 9:
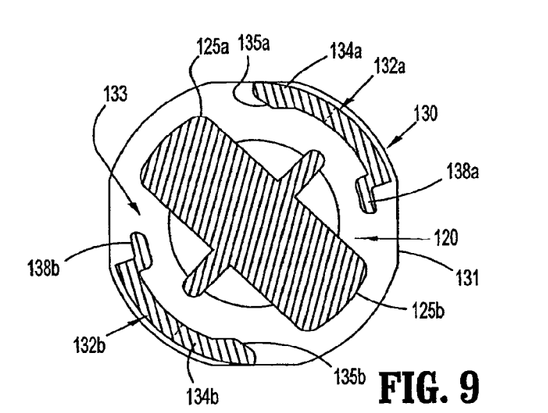
FIGS. 9-11 are plan views illustrating the attachment of the plunger rod to the plug of the detachable plunger rod syringe of FIGS. 1 and 2.
Figure 10:
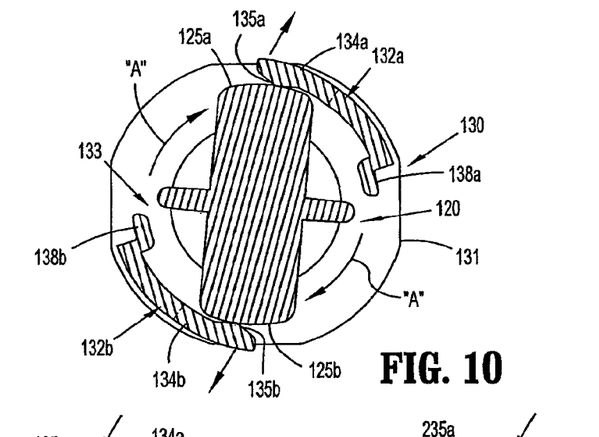
Figure 11:
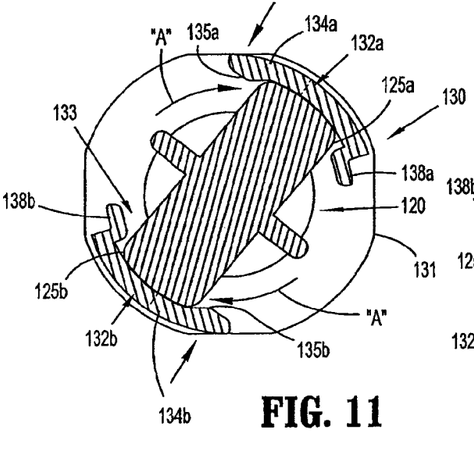
Figure 11A:
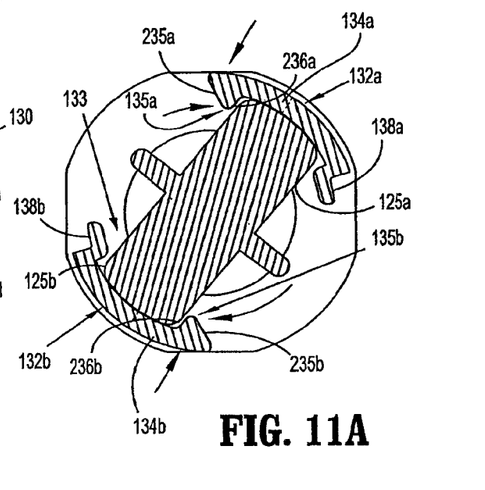
FIG. 11A is a plan view illustrating the attachment of the plunger rod to the plug of FIG. 7A.

Turning now to FIGS. 3-5 and 9-11, with plug 130 either disposed within cavity 110c of syringe barrel 110 or separated therefrom, plug 130 is selectively connectable to distal end 123 of plunger rod 120. Attachment of plug 130 to distal end 123 of plunger rod 120 entails, as seen in FIGS. 3 and 9, aligning tabs 125a, 125b between the space defined by the pair of uprights 132a, 132b extending from base wall 131 of plug 130. With tabs 125a, 125b so aligned, as seen in FIG. 4, plunger rod 120 and plug 130 are approximated so that tabs 125a, 125b are proximate base wall 131 within space 133. Plunger rod 120 is then rotated, as seen in FIGS. 5 and 10, in the direction of arrows "A", towards shoulders 135a, 135b of fingers 134a, 134b. With continued reference to FIGS. 5 and 10, as well as FIG. 11, plunger rod 120 is rotated in the direction of arrows "A", until shoulders 135a, 135b snap over tabs 125a, 125b, respectively. Rotation of plunger rod 120 relative to plug 130 is terminated or further prevented when tabs 125a, 125b engage stops 138a, 138b (see FIGS. 7 and 9-11) projecting inward from respective uprights 132a, 132b.

With plug 130 supported on distal end 123 of plunger rod 120, plunger rod 120 is prevented from axially disengaging from plug 130 by lips 139a, 139b (see FIGS. 3-5 and 13) extending from respective uprights 132a, 132b. In this manner, if plunger rod 120 is moved in a proximal direction relative to plug 130, plug 130 will concomitantly move with plunger rod 120 due to the abutment of tabs 125a, 125b against respective lips 139a, 139b of plug 130.

Plunger rod 120 is separated from plug 130 by rotating plunger rod 120 in a direction opposite to arrows "A", relative to plug 130, to move tabs 125a, 125b past shoulders 135a, 135b and into the space between uprights 132a, 132b, respectively.

Figure 12:
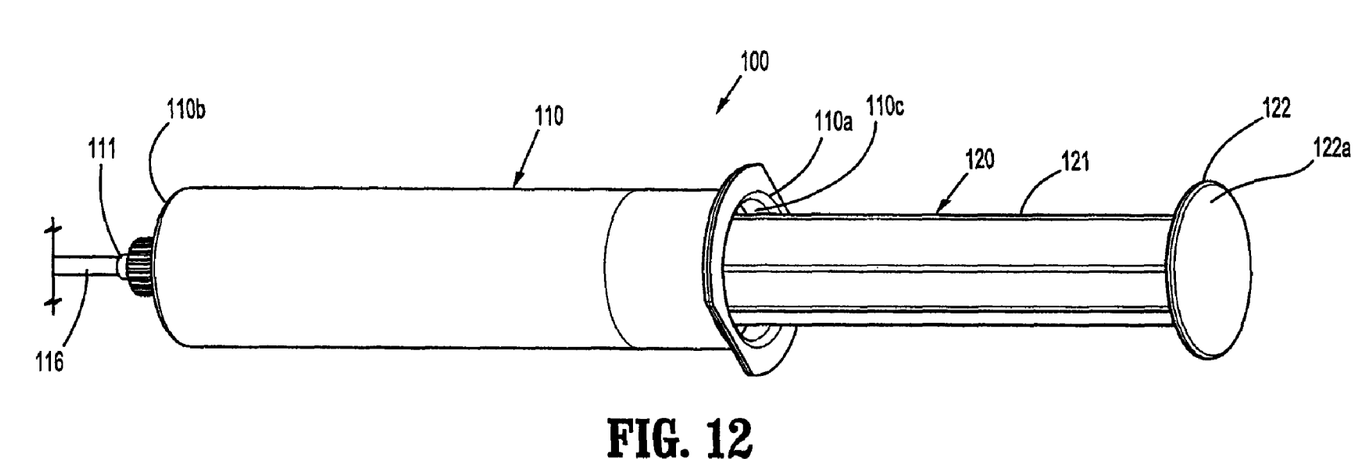
FIG. 12 is a perspective view of an assembled detachable plunger rod syringe of FIGS. 1 and 2.
Figure 13:
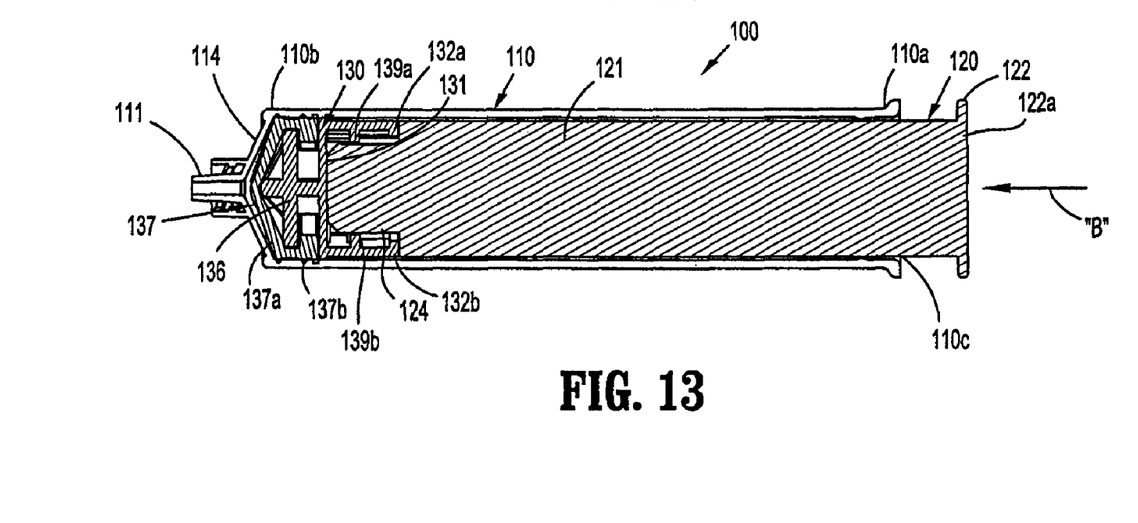
FIG. 13 is a longitudinal, cross-sectional view of the detachable plunger rod syringe of FIGS. 1 and 2, illustrating the plug fully advanced through the syringe barrel by the plunger rod.

As seen in FIGS. 12 and 13, with plunger rod 120 attached to plug 130 and with plug 130 disposed within cavity 110c of syringe barrel 110, plunger rod 120 is moved in the direction of arrow "B" (i.e., toward barrel tip 111). As plunger rod 120 is moved in the direction of arrow "B", fluid contained within cavity 110c of syringe barrel 110 is expelled or dispensed through syringe tube 116.

Turning now to FIGS. 14-21, a plunger rod 320 and a plug 330, in accordance with another embodiment of the present disclosure, for use with syringe barrel 110 (see FIGS. 1 and 2) is shown and described below. Plunger rod 320 and plug 330 are each substantially similar to respective plunger rod 120 and plug 130 and thus will only be described in detail herein to the extent necessary to identify differences in construction and operation.

As seen in FIGS. 14-19, plunger rod 320 includes an elongate plunger shaft 321 configured and dimensioned for slidable disposition within a syringe barrel (similar to syringe barrel 11 shown in FIGS. 1, 2, 8, 12 and 13 above). Plunger shaft 321 includes a proximal end 322 which extends out of a proximal end of the syringe barrel and defines a finger engagement surface. Plunger shaft 321 includes a distal end 323 disposable within the syringe barrel.

Distal end 323 of plunger shaft 321 is configured and dimensioned to support plug 330 thereon. Distal end 323 includes a hub 324 extending distally therefrom and a pair of tabs 325a, 325b extending radially outwardly from hub 324. Hub 324 defines a planar distal surface 326.

Figure 17:
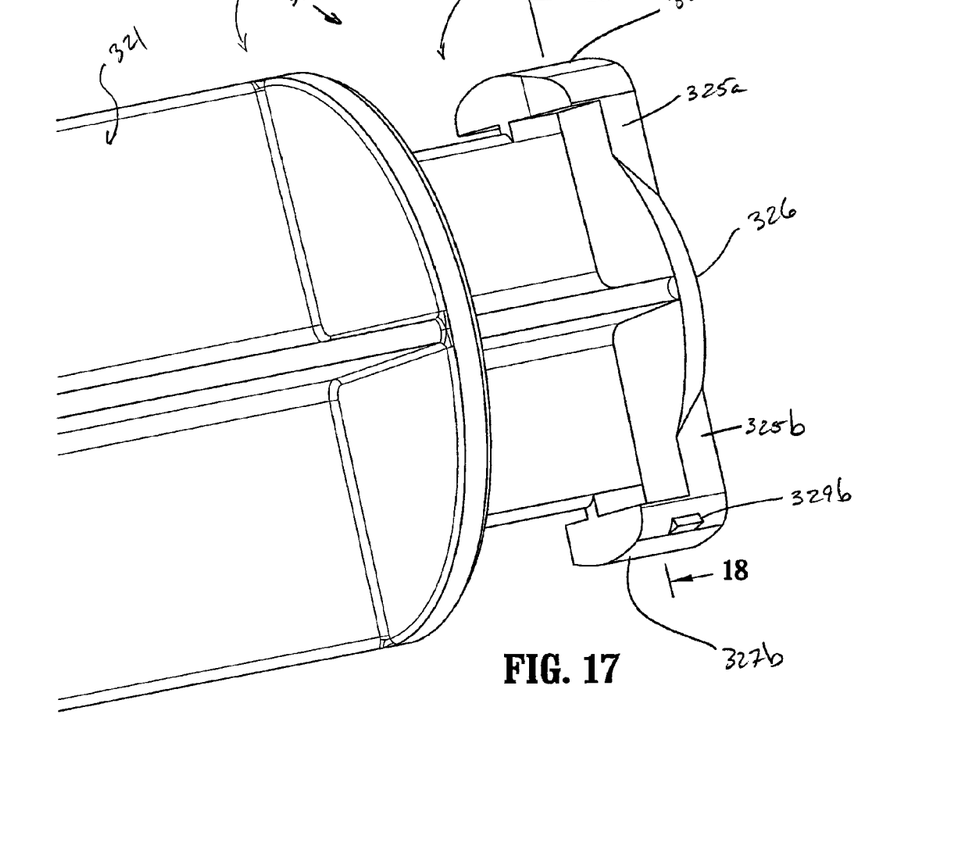
FIG. 17 is an enlarged perspective view of the indicated area of detail of FIG. 16.
Figure 18:
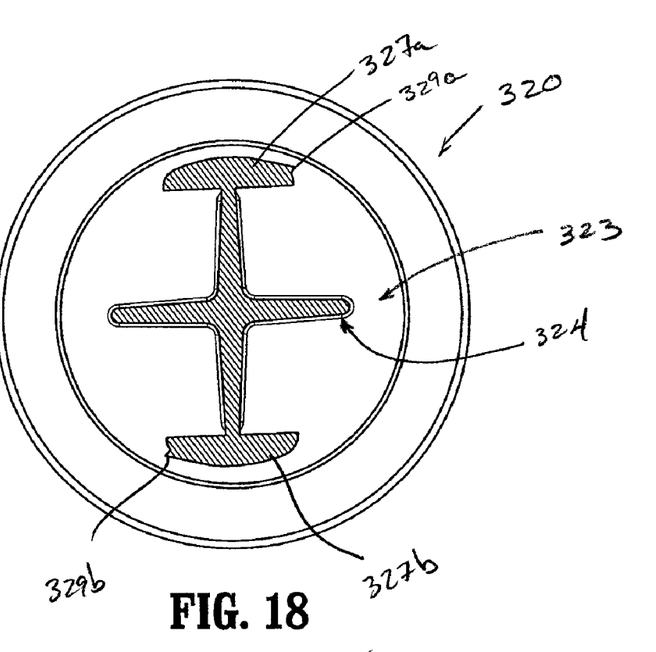
FIG. 18 is a cross-sectional view of a distal end of the plunger rod of FIGS. 14-17, as taken through 18-18 of FIG. 17.
Figure 19:
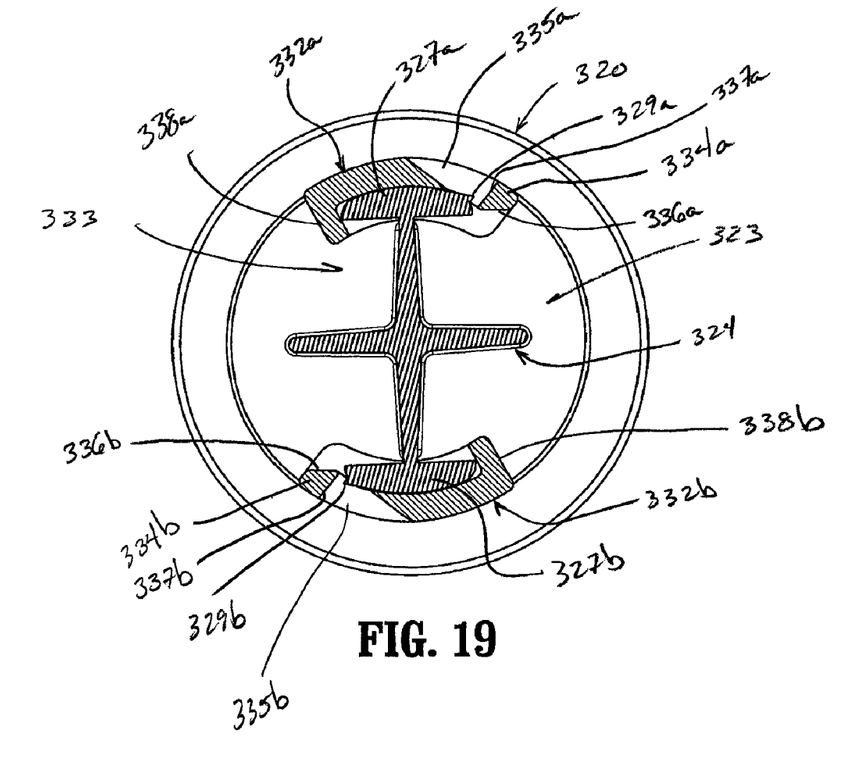
FIG. 19 is a cross-sectional view of the plunger rod and plug of FIGS. 14 and 15, as taken through 19-19 of FIG. 15.

Each tab 325a, 325b has a length which extends radially beyond an outer diameter of hub 324 and which length does not extend radially beyond an inner diameter of a cavity of the syringe barrel. Each tab 325a, 325b includes a respective wall, ear or wing 327a, 327b extending in a substantially proximal direction from an outer end thereof. Each wall 327a, 327b includes a respective stop member 329a, 329b or the like projecting from an outer surface thereof. As seen in FIGS. 17-19, stop members 329a, 329b may be in the form of ramps or the like.

Figure 14:
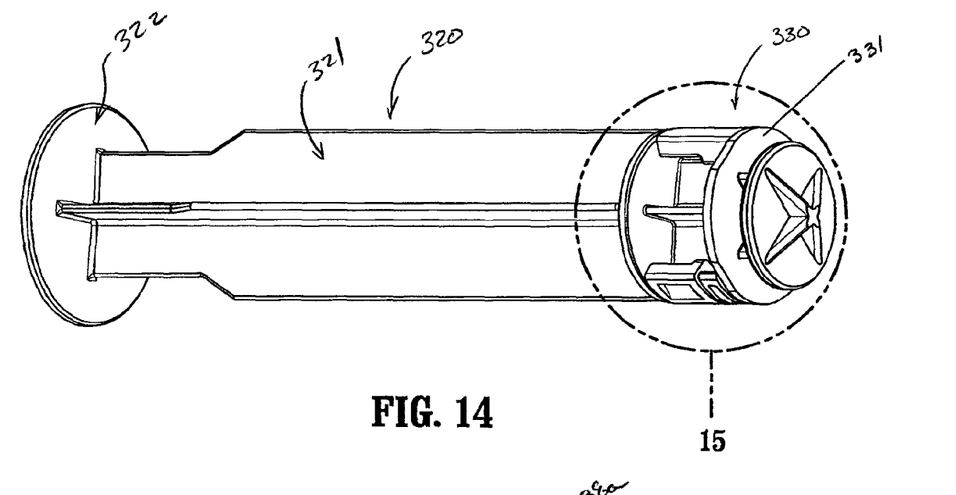
FIG. 14 is a perspective view of a plunger rod and plug, according to another embodiment of the present disclosure, shown in an assembled condition.
Figure 15:
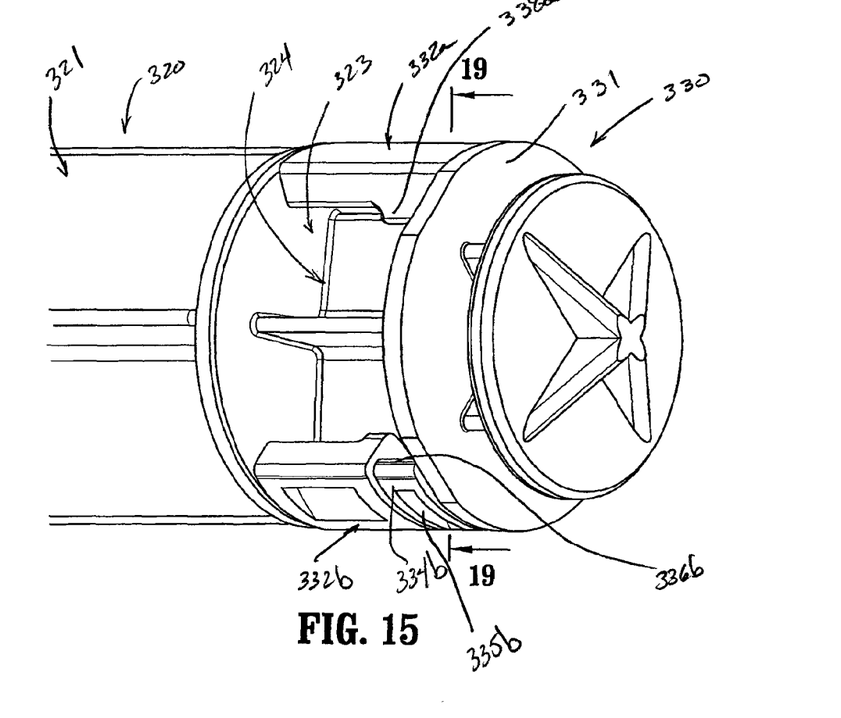
FIG. 15 is an enlarged perspective view of the indicated area of detail of FIG. 14.
Figure 16:
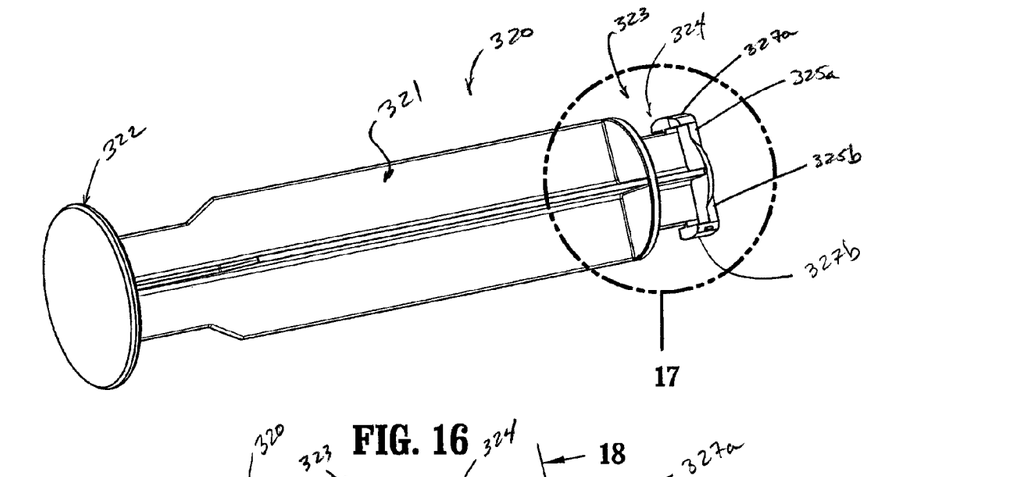
FIG. 16 is a rear perspective view of the plunger rod of FIGS. 14 and 15.

As seen in FIGS. 14, 15 and 19, plug 330 includes a base wall 331 having a pair of spaced apart uprights 332a, 332b extending from a first surface thereof. Uprights 332a, 332b define a space 333 therebetween. Each upright 332a, 332b includes a resilient finger 334a, 334b, respectively formed therein. Each resilient finger 334a, 334b includes a recess 335a, 335b, respectively, formed therein at a location proximate a free end thereof. Recesses 335a, 335b are each configured to receive respective stop members 329a, 329b of plunger rod 320 during attachment of plug 330 to distal end 323 of plunger rod 320.

As seen in FIG. 19, each finger 334a, 334b defines a sloping distal profile 336a, 336b, respectively, to facilitate attachment of plug 330 to plunger rod 320, and each recess 335a, 335b defines a substantially orthogonal distal wall 337a, 337b, respectively, which engages stop members 329a, 329b of plunger rod 320 to inhibit detachment of plug 330 from plunger rod 320. In this manner, plug 330 may be relatively easily attached to plunger rod 320, however, plug 330 may not be relatively easily detached from plunger rod 320.

Figure 20:
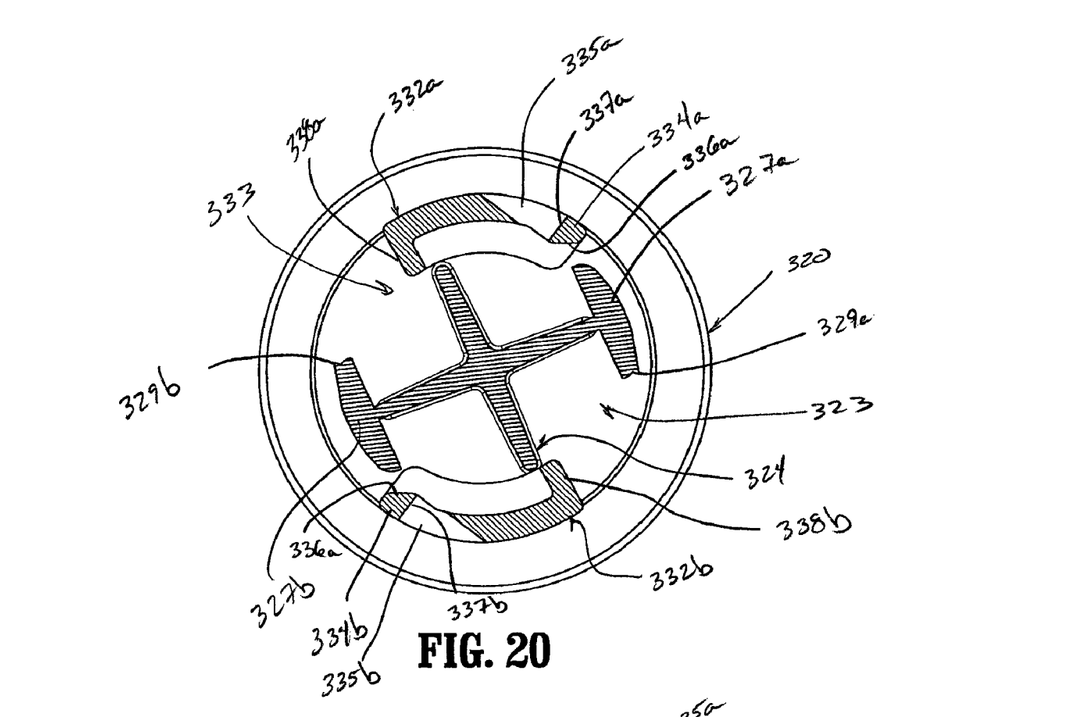
FIGS. 20 and 21 is a cross-sectional view of the plunger rod and plug of FIGS. 14 and 15, as taken through 19-19 of FIG. 15, illustrating the connection of the plug to the plunger rod.
Figure 21:
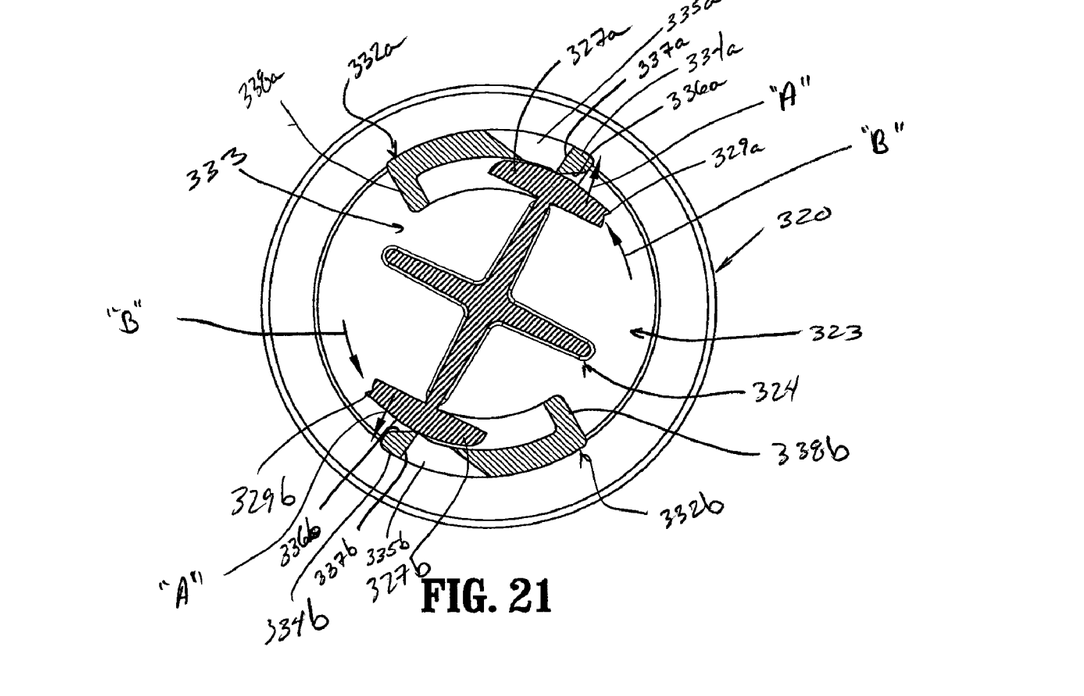

Turning now to FIGS. 20 and 21, in attaching plug 330 to the distal end of plunger rod 320, as plunger rod 320 is rotated relative to plug 330 (as indicated by arrows "B" of FIG. 21), tabs 325a, 325b and/or walls 327a, 327b cam against the respective distal surfaces of fingers 334a, 334b to radially extend fingers 334a, 334b (as indicated by arrows "A" of FIG. 21) and allow stop members 329a, 329b to snap-fit into respective recesses 335a, 335b.

Rotation of plug 330 relative to plunger rod 320 is terminated when tabs 325a, 325b and/or walls 327a, 327b engage stops 338a, 338b projecting inward from respective uprights 332a, 332b, as seen in FIG. 19.

Base wall 331, uprights 332a, 332b and/or support element 336 may be formed of a semi-rigid material, such as polypropylene. Plunger tip 337 may be formed of a resilient and/or elastomeric material, such as, for example, rubber or silicone rubber.

It is contemplated that uprights 132a, 132b of plug 130 and uprights 332a, 332b of plug 330 are dimensioned, e.g., have a length sufficient, so as to maintain plugs 130, 330 and respective plunger rods 120, 320 axially aligned with one another during operation of syringes 100, 300. In this manner, an operable seal is maintained between resilient plunger tips 137, 337 and syringe barrel 110 during axial translation of plunger rods 120, 320 through syringe barrel 110.

It is further contemplated that plugs 130, 330 may be configured in such a manner as to inhibit "nesting", that is, interlocking, of one plug with another when plugs are grouped for storage or transport prior to assembly. For example, any recesses formed in a rear or proximal surface of each plug, to accommodate support element 136, may be configured and dimensioned so as to prevent nesting of a front or distal surface of another plug therein.

It is still further contemplated that the configurations and/or dimensions of tabs 125a, 125b of plunger rod 120 and/or walls 327a, 327b of plunger rod 320, in combination with the location, configuration and/or dimensions of lips 139a, 139b (see FIGS. 3-5, 8 and 13) of plugs 130, 330 is such that axial movement of plunger rods 120, 320 relative to respective plugs 130, 330 is reduced or minimized. For example, it is contemplated that proximal surfaces of tabs 125a, 125b or proximal surfaces of walls 327a, 327b and/or distal surfaces of lips 139a, 139b may be ramped or angled. In this manner, as plunger rod 120, 320 is rotated relative to respective plugs 130, 330 results in a wedge or binding effect therebetween. It is further contemplated that at least proximal surfaces of tabs 125a, 125b or proximal surfaces of walls 327a, 327b and/or distal surfaces of lips 139a, 139b may include crush ribs or any other suitable structure capable of reducing the gap distance or tolerance between tabs 125a, 125b of plunger rod 120 or walls 327a, 327b of plunger rod 320 and lips 139a, 139b.

Although particular embodiments of the invention have been described in detail for purposes of illustration, various modifications and enhancements may be made without departing from the spirit and scope of the inventions. Accordingly, the invention is not to be limited except as by the appended claims.

What is claimed is:

1. A syringe, comprising:
    a syringe barrel having a distal end, a proximal end and defining a cavity therebetween;
    a plunger rod slidably disposed within the cavity of the syringe barrel, the plunger rod including a plunger shaft having a non-depressible hub extending distally from a distal end thereof, the hub includes at least two non-movable spaced apart tabs with respect to the non-depressible hub, the two non-movable spaced apart tabs integrally formed and extending outwardly from a non-distal end of the hub and a spacer disposed at a distal end of the hub, the at least two spaced apart tabs being spaced a distance from the spacer; and
    a plug configured for slidable disposition in the cavity of the syringe barrel and configured for selective, detachable, and rotatable connection to the at least two spaced apart tabs of the hub, the plug including:
        a base wall having at least two spaced apart uprights extending from diametrically opposing sections of a first side thereof, wherein each upright includes a resilient finger formed therein, each resilient finger is configured to snap-fit engage a respective tab of the plunger rod during connection of the plug to the plunger rod, wherein the at least two spaced apart uprights fully receive the hub, the at least two spaced apart tabs and the spacer therebetween; and
        a plunger tip supported on a second side of the base wall, opposite the first side, and being configured to form a substantially fluid tight seal with an inner surface of the cavity of the syringe barrel
    wherein during connection of the plug to the plunger rod, and after insertion into the syringe barrel, the at least two spaced apart resilient fingers contacting an inner surface of the syringe barrel thereby limiting a radially outward deflection thereof.

2. The syringe according to claim 1, wherein each resilient finger includes a shoulder extending inwardly therefrom.

3. The syringe according to claim 2, wherein each shoulder includes a sloping distal surface.

4. The syringe according to claim 2, wherein each shoulder includes a substantially orthogonal surface formed therein for inhibiting a respective tab of the plunger rod from moving therebeyond, whereby disconnection of the plug from the plunger rod is prevented.

5. The syringe according to claim 4, wherein each resilient finger defines a recess formed in an inner surface thereof and defining the substantially orthogonal surface.

6. The syringe according to claim 4, wherein at least one tab includes a stop member configured to engage the substantially orthogonal surface of a respective resilient finger.

7. The syringe according to claim 1, wherein the tabs of the plunger rod are diametrically opposed from one another.

8. The syringe according to claim 1, wherein tabs of the plunger rod extend substantially radially outward from the hub.

9. The syringe according to claim 1, wherein the tabs and the hub of the plunger rod define a substantially planar distal surface.

10. The syringe according to claim 1, wherein at least one upright includes a stop extending from an inner surface thereof for preventing movement of the tabs of the plunger rod as the plunger rod is rotated with respect to the plug.

11. The syringe according to claim 1, wherein the plunger tip is formed of an elastomeric material.

12. The syringe according to claim 1, wherein the base wall and the uprights of the plug are formed from polypropylene.

13. The syringe according to claim 1, wherein the plug is connected to the distal end of the plunger rod in a bayonet-type connection.

14. A plunger rod assembly for use with a syringe barrel, comprising:
    a plunger rod slidably disposable within the syringe barrel, the plunger rod including a hub extending distally from a distal end thereof and at least two spaced apart tabs extending outwardly therefrom and a spacer disposed at a distal end of the hub, the at least two spaced apart tabs being spaced a distance from the spacer; and
    a plug configured for slidable disposition in the syringe barrel and configured for selective connection to the plunger rod via a bayonet-type engagement, the plug including:
        a base wall having at least two spaced apart resilient fingers supported on a first side thereof, wherein each resilient finger is configured to snap-fit engage a respective tab of the plunger rod during connection of the plug to the plunger rod; and
        a plunger tip supported on a second side of the base wall, opposite the first side, and being configured to form a substantially fluid tight seal with an inner surface of the syringe barrel;
    wherein the at least two spaced apart tabs are dimensioned for approximation in a linear direction when axially aligned and for disposition between the at least two spaced apart resilient fingers during connection of the plunger rod to the plug;

wherein in a first orientation, a longitudinal axis extending through the spaced apart tabs is aligned with an axis extending between the spaced apart resilient fingers and in a second orientation, the longitudinal axis extending through the spaced apart tabs is radially offset relative to the axis extending between the spaced apart resilient fingers; and wherein during connection of the plug to the plunger rod, while the plug is disposed in the syringe barrel, the at least two spaced apart resilient fingers are bound by an inner surface of the syringe barrel thereby limiting a radially outward deflection thereof.

15. The plunger rod assembly according to claim 14, wherein each resilient finger includes a shoulder extending inwardly therefrom.

16. The plunger rod assembly according to claim 15, wherein each shoulder includes a substantially orthogonal surface formed therein for inhibiting a respective tab of the plunger rod from moving therebeyond, whereby disconnection of the plug from the plunger rod is prevented.

17. The plunger rod assembly according to claim 16, wherein each resilient finger defines a recess formed in an inner surface thereof and defining the substantially orthogonal surface.

18. The plunger rod assembly according to claim 16, wherein at least one tab includes a stop member configured to engage the substantially orthogonal surface of a respective resilient finger.

19. The plunger rod assembly according to claim 14, wherein at least one upright includes a stop extending from an inner surface thereof for preventing movement of the tabs of the plunger rod as the plunger rod is rotated with respect to the plug.

20. The plunger rod assembly according to claim 14, wherein the hub is a non-depressible hub including the at least two non-movable spaced apart tabs being integrally formed at a distal end of the non-depressible hub.

21. A syringe, comprising:
a syringe barrel having a distal end, a proximal end and defining a cavity therebetween;
a plunger rod slidably disposable within the cavity of the syringe barrel, the plunger rod including a plunger shaft having a hub extending distally from a distal end thereof, the hub includes a pair of spaced apart tabs extending outwardly therefrom; and
a plug configured for slidable disposition in the cavity of the syringe barrel and configured for selective connection to the distal end the plunger rod via a bayonet-type engagement, the plug including:
a base wall having at least two spaced apart resilient fingers supported on a first side thereof, wherein each upright includes a resilient finger formed therein, each resilient finger is configured to snap-fit engage a respective tab of the plunger rod as the plunger rod is rotated with respect to the plug when the pair of spaced apart tabs are in registration with the respective resilient fingers; and
a plunger tip supported on a second side of the base wall, opposite the first side, and being configured to form at least a substantially fluid tight seal with an inner surface of the cavity of the syringe barrel;
wherein the plunger rod is configured to rotate in a first direction relative to the plug until the spaced apart tabs of the plunger rod engage a stop and establish a connection therebetween, and wherein the plunger rod is configured to rotate in a second direction relative to the plug to disconnect the plunger rod from the plug;
wherein in a first orientation, a longitudinal axis extending through the pair of spaced apart tabs is aligned with an axis extending between the spaced apart uprights and in a second orientation, the longitudinal axis extending through the pair of spaced apart tabs is radially offset relative to the axis extending between the spaced apart uprights; and
wherein during connection of the plug to the plunger rod, while the plug is disposed in the syringe barrel, the at least two spaced apart resilient fingers are bound by an inner surface of the syringe barrel thereby limiting a radially outward deflection thereof.

* * * * *